United States Patent
Clarke

(10) Patent No.: US 9,687,395 B2
(45) Date of Patent: Jun. 27, 2017

(54) REPOSITIONABLE MOISTURE MANAGEMENT MATERIAL THAT CREATES A BARRIER TO SKIN-ON-SKIN CONTACT

(71) Applicant: Mountain Park Music, Inc., Studio City, CA (US)

(72) Inventor: Miriam S. Clarke, Studio City, CA (US)

(73) Assignee: Mountain Park Music, Inc., Studio City, CA (US)

( * ) Notice: Subject to any disclaimer, the term of this patent is extended or adjusted under 35 U.S.C. 154(b) by 0 days.

(21) Appl. No.: 15/049,673

(22) Filed: Feb. 22, 2016

(65) Prior Publication Data
US 2016/0242972 A1    Aug. 25, 2016

Related U.S. Application Data

(60) Provisional application No. 62/118,578, filed on Feb. 20, 2015.

(51) Int. Cl.
*A41C 3/12*    (2006.01)
*A61F 13/74*    (2006.01)
(Continued)

(52) U.S. Cl.
CPC .............. *A61F 13/74* (2013.01); *A41B 17/00* (2013.01); *A41B 17/005* (2013.01); *A41C 3/12* (2013.01);
(Continued)

(58) Field of Classification Search
CPC .............. A41C 3/04; A41C 3/12; A41D 27/12
(Continued)

(56) References Cited

U.S. PATENT DOCUMENTS

| 356,090 A | * | 1/1887 | Bebb | ...................... D01G 15/46 |
| | | | | 19/106 R |
| 1,838,013 A | | 3/1931 | Tisdall | |

(Continued)

FOREIGN PATENT DOCUMENTS

WO    2012087292    6/2012

OTHER PUBLICATIONS

PCT/US16/18923; International Search Report and Written Opinion dated Jun. 21, 2016 (11 pgs).

*Primary Examiner* — Gloria Hale
(74) *Attorney, Agent, or Firm* — Gearhart Law LLC

(57) ABSTRACT

An article of clothing can be used to reduce or prevent the occurrence of prolonged skin-on-skin contact, rashes, irritation, intertrigo, infections, discomfort, or chaffing. Such an article of clothing has a moisture management material made up of at least an outer layer, an inner layer, and a tab. The moisture management material is attached to a portion of the article of clothing via a tab of the moisture management material. The moisture management material may be of various shapes and sizes and preferably fits within a prescribed area of the article of clothing. The moisture management material may be variably positioned within the article of clothing to provide differing results such as additional support and/or moisture absorbing or moisture moving where necessary. Preferably the article of clothing is a brassiere but may be a shirt, diaper, pants, socks, panties, or other undergarments.

13 Claims, 5 Drawing Sheets

(51) Int. Cl.
*A41B 17/00* (2006.01)
*A41C 3/14* (2006.01)
*A41D 27/13* (2006.01)
*A41D 31/02* (2006.01)
*A61L 15/24* (2006.01)
*A61L 15/26* (2006.01)
*A61L 15/30* (2006.01)
*A41D 27/12* (2006.01)

(52) U.S. Cl.
CPC ............... *A41C 3/14* (2013.01); *A41D 27/12* (2013.01); *A41D 27/13* (2013.01); *A41D 31/02* (2013.01); *A61L 15/24* (2013.01); *A61L 15/26* (2013.01); *A61L 15/30* (2013.01); *A41B 2400/34* (2013.01); *A41D 2400/60* (2013.01)

(58) Field of Classification Search
USPC ........................................ 450/37, 54–57, 81
See application file for complete search history.

(56) References Cited

U.S. PATENT DOCUMENTS

| | | | |
|---|---|---|---|
| 2,543,721 A | 12/1950 | Marshall | |
| 2,598,003 A | 5/1952 | Leo et al. | |
| 2,661,470 A | 12/1953 | Day | |
| 2,869,552 A | 1/1959 | Smith | |
| 3,260,261 A | 7/1966 | Gallovich | |
| 3,356,090 A * | 12/1967 | Plantinga | A61F 13/141 |
| | | | 450/37 |
| 3,934,593 A * | 1/1976 | Mellinger | A41C 3/065 |
| | | | 428/355 R |
| 4,074,721 A * | 2/1978 | Smits | A61F 13/141 |
| | | | 450/37 |
| 5,217,447 A | 6/1993 | Gagnon | |
| 5,334,082 A | 8/1994 | Barker | |
| 5,716,255 A * | 2/1998 | Abercrombie | A41C 3/12 |
| | | | 2/267 |
| 5,951,366 A | 9/1999 | Stevens | |
| 5,980,359 A * | 11/1999 | Brown | A41C 3/12 |
| | | | 450/14 |
| 5,998,693 A * | 12/1999 | Zagame | A61F 13/145 |
| | | | 450/81 |
| 6,203,399 B1 * | 3/2001 | Hackney | A41C 3/00 |
| | | | 2/267 |
| 6,264,530 B1 * | 7/2001 | Cosentino | A41C 3/12 |
| | | | 2/267 |
| 6,406,353 B1 | 6/2002 | Harper | |
| 6,787,682 B2 | 9/2004 | Gilman | |
| 7,001,241 B2 * | 2/2006 | Gorringe | A61F 13/141 |
| | | | 450/37 |
| 7,278,899 B2 | 10/2007 | Davis | |
| 7,323,243 B2 | 1/2008 | Baychar | |
| 7,404,752 B1 * | 7/2008 | Karon | A41C 3/12 |
| | | | 2/53 |
| 7,442,110 B2 | 10/2008 | Gaudet et al. | |
| 7,794,304 B2 | 9/2010 | Frye | |
| 7,815,487 B2 | 10/2010 | Warren | |
| 7,905,763 B1 * | 3/2011 | Frank | A41D 27/12 |
| | | | 450/37 |
| 7,976,357 B1 | 7/2011 | Riley | |
| 8,075,367 B2 | 12/2011 | Taylor | |
| 8,657,643 B2 | 2/2014 | Perez | |
| 8,911,416 B2 * | 12/2014 | Johnson | A41D 27/12 |
| | | | 450/37 |
| 2003/0220048 A1 | 11/2003 | Toro et al. | |
| 2004/0226069 A1 * | 11/2004 | Reeves | A41D 27/13 |
| | | | 2/55 |
| 2008/0177214 A1 | 7/2008 | Robertsson et al. | |
| 2009/0299252 A1 * | 12/2009 | O'Neill | A61F 13/145 |
| | | | 602/48 |
| 2010/0101586 A1 | 4/2010 | Frye | |
| 2011/0092935 A1 | 4/2011 | Hann | |
| 2011/0259349 A1 | 10/2011 | McDonnell | |
| 2012/0129428 A1 * | 5/2012 | Taylor | A41C 3/04 |
| | | | 450/37 |
| 2013/0059498 A1 | 3/2013 | Hersh | |
| 2013/0104914 A1 | 5/2013 | Stewart | |
| 2013/0116612 A1 | 5/2013 | Stephan | |
| 2014/0302745 A1 | 10/2014 | Golubovic et al. | |
| 2014/0364825 A1 * | 12/2014 | Krasikoff | A61F 13/45 |
| | | | 604/374 |

\* cited by examiner

REPOSITIONABLE MOISTURE MANAGEMENT MATERIAL THAT CREATES A BARRIER TO SKIN-ON-SKIN CONTACT

CLAIM OF PRIORITY

This application claims priority to U.S. Application Ser. No. 62/118,578 filed on Feb. 20, 2015, the contents of which are herein fully incorporated by reference in its entirety.

FIELD OF THE EMBODIMENTS

The present invention and its embodiments relate to protective devices that provide relief and prevention to users who experience discomfort due to prolonged skin-on-skin contact and/or perspiration throughout the course of a day and/or night, namely a medical device that may be coupled to articles of clothing thereby providing a barrier to skin-on-skin contact to alleviate chaffing, rashes, infections, intertrigo, soreness, irritation, discomfort, and the potential embarrassment caused by these conditions.

BACKGROUND OF THE EMBODIMENTS

Excessive moisture in a variety of scenarios can cause numerous undesirable effects. Often, places susceptible to such excessive moisture content are breeding grounds for bacteria, funguses, and various other types of pathogens. When these locations are persistent on the human body various afflictions such as intertrigo and bacterial infections often occur jeopardizing the health of the host body.

Historically, men and women alike have attempted, utilizing various methodologies, to alleviate, prevent, or otherwise limit the wetness and odor caused by perspiration. In humans, excessive moisture (i.e. perspiration) can be trapped in any number of crevices along the human body. This increased moisture level can then, in turn, be exacerbated by heat (including body heat), a lack of air circulation, and friction between places of skin-on-skin contact (i.e. skin folds). Often such a combination of factors results in tenderness, redness, friction, and intertrigo amongst other afflictions. These conditions can then lead to secondary infections caused by funguses, bacteria, yeasts, and the like. Once these ailments have set in, treatment is typically seen in the form of creams, ointments, powders, and anti-inflammatories, anti-fungals, and even antibiotics in extreme cases.

There are a number of options available to help alleviate, avoid, or reduce such ailments including: avoiding tight clothing, losing weight, and wearing a brassiere or other garment with sufficient support. However, these steps are not necessarily practical or effective for all of those who suffer from these conditions as there are a wide variety of reasons and medical issues that can cause the aforementioned ailments.

For example, for many the "underbust," or area below/underneath the breasts is particularly problematic, especially for those women who are overweight or have particularly large breasts. Yet, women with "average" breasts are not exempt from this condition and should be cognizant of the implications of such an affliction. Typically, women attempt to combat this problem and discomfort by using various objects of relief such as but not limited to napkins, tissues, gauze, anti-fungals, toilet paper, and other suggested remedies, and the like only to be greeted with tepid results. Further, when such remedies are used one must be fearful of losing the placed objects of relief and being subjected to embarrassment due to the unfixed nature of these items.

Additionally, in other settings, older adults may have difficulties with incontinence or are bed ridden which can lead to similar symptoms around the buttocks and genital region, especially the inner thighs and between the buttocks. Even still, overweight individuals may have a number of skin folds which require constant cleaning and moisture absorbing powders to prevent excess sweating and moisture build up.

Thus, there is a need for the moisture management material to be integrated with a garment, medical device, or article of clothing that helps to reduce or move away excess moisture and create a barrier to skin-on-skin contact to prevent or limit the frequency of the aforementioned and other not named afflictions. The present invention and its embodiments meets and exceeds these objectives. The present invention uses at least one moisture management material strategically located and capable of being variably positioned to further create a barrier to skin-on-skin contact. This allows one to target problem areas and increase the relief from discomfort.

Review of Related Technology:

U.S. Pat. No. 7,794,304 pertains to a foldable one-piece insert worn between the brassiere and the body having irritation reducing and/or absorbent material portions which line the brassiere cup and that lie under the supported breast, and portions which extends toward the torso rear under the brassiere side straps and a portion extending below the brassiere line along the torso. The invention further includes a material tab disposed between the material portions lining the brassiere cups, which can optionally be worn up to bridge the area between the brassiere cups for added protection, comfort and absorption of perspiration, or be folded down and out of sight when worn with lower cut neckline outer garments.

U.S. Pat. No. 5,980,359 pertains to a brassiere barrier device comprising a flexible, substantially flat absorptive protective band worn on an abdomen of a woman's body. A top edge of the band extends under the breasts and a lower border at the cups of a brassiere, so as to prevent dermal irritation and lesions caused by heat, moisture and chaffing associated with use of the brassiere.

U.S. Patent Application 2013/0104914 pertains to a brassiere accessory for eliminating or substantially reducing the discomfort, chaffing, pain, rash, intertrigo, and infections caused by pressure of a woman's brassiere cup rim against her chest, and by perspiration trapped between the woman's breast and chest.

Various devices are known in the art. However, their structure and means of operation are substantially different from the present disclosure. The other inventions fail to solve all the problems taught by the present disclosure. The present invention provides for a reconfigurable moisture management material that can be placed to target areas of the body susceptible to moisture buildup. In some embodiments, such as when applied to a brassiere, the moisture management material can be folded into the cup of the brassiere providing increased levels of support and lifting of the breast. At least one embodiment of this invention is presented in the drawings below and will be described in more detail herein.

SUMMARY OF THE EMBODIMENTS

Generally, the present invention and its embodiments provide for an article of clothing to alleviate the occurrence buildup of excess moisture or prolonged skin-on-skin contact which can lead to recurring rashes, irritation, intertrigo, discomfort, infections, or chaffing. The article of clothing or garment has at least one and preferably multiple pieces of moisture management material strategically positioned and coupled thereto. The moisture management material can be shaped to conform to certain garments and/or locations on the body. Further, the moisture management material is capable of being removed and cleaned and/or replaced in addition to being repositionable.

In one embodiment, the present invention is a system to alleviate the occurrence of prolonged skin-on-skin contact, rashes, irritation, intertrigo, infections, discomfort, or chaffing or any combination thereof, the article of clothing comprising: a material forming a wearable garment; and a moisture management material comprising at least an outer layer, an inner layer, and a tab being coupled to a portion of the length of material, wherein the tab extending from the moisture management material providing a surface to couple the moisture management material to the wearable garment.

In another embodiment there is a medical accessory to alleviate the occurrence of prolonged skin-on-skin contact, rashes, irritation, intertrigo, infections, discomfort, or chaffing or any combination thereof, the medical accessory comprising: a moisture management material having an inner layer, an outer layer, and at least a first edge and a second edge, wherein the first edge is a flat edge and the second edge is a flat edge or a curved edge; and a tab extending from the moisture management material sized to enable the medical accessory to be coupled to an article of clothing.

In another embodiment of the invention there is a brassiere accessory comprising: a moisture management material having a flat edge and an additional flat or curved edge, wherein the moisture management material has at least an inner layer and an outer layer, wherein the inner layer is bounded on both sides by the outer layer; and a tab extending from the moisture management material sized to enable the brassiere accessory to be coupled to a brassiere, wherein the moisture management material is configured to be positioned into a cup of the brassiere or positioned to extend outwardly from the cup of the brassiere; and wherein if the brassiere has an underwire the tab is coupled to the brassiere above and/or below the underwire, and if the brassiere has no underwire the tab is coupled to a fabric strip of the brassiere.

In another embodiment there is a pair of underwear having a length of material configured to cover at least a part of a genital region of a user; and a moisture management material comprising at least an outer layer and an inner layer and being coupled to a portion of the length of material, wherein the moisture management material has a flat edge and an additional flat or curved edge, wherein at least one of the edges has a tab or tabs extending therefrom providing a surface to couple the moisture management material to the wearable garment; wherein the moisture management material is coupled to the pair of underwear along the waistline or along leg openings or other openings or along the side seams or a combination thereof.

In yet another embodiment of the present invention there is a shirt having a length of material configured to cover at least a torso of a user; and at least one piece of the moisture management material comprising at least an outer layer and an inner layer and being coupled to a portion of the length of material, wherein the moisture management material has a flat edge and an additional flat or curved edge, wherein at least one of the edges has a tab or tabs extending therefrom providing a surface to couple the moisture management material to the wearable garment; wherein the moisture management material is coupled to an interior surface of the shirt in the chest region and is capable of being positioned in areas subjected to skin-on-skin contact.

In yet another embodiment of the present invention there is a diaper or other full coverage undergarment having a length of material configured to cover a genital region of a user; and a moisture management material comprising at least an outer layer and an inner layer and being coupled to a portion of the length of material, wherein the moisture management material has a flat edge and an additional flat or curved edge, wherein at least one of the edges has a tab or tabs extending therefrom providing a surface to couple the moisture management material to the wearable garment; wherein the moisture management material is coupled to the diaper along leg openings or the rear central portion of the diaper or a combination thereof.

In general, the present invention succeeds in conferring the following, and others not mentioned, benefits and objectives.

It is an object of the present invention to provide an article of clothing that prevents or limits prolonged skin-on-skin contact.

It is an object of the present invention to provide an article of clothing that prevents or limits buildup of excess moisture.

It is an object of the present invention to provide an article of clothing that has a disposable or non-disposable moisture management material coupled thereto.

It is an object of the present invention to provide an article of clothing that alleviates irritation, swelling, chaffing, redness, soreness, intertrigo, discomfort, infections, and the like.

It is an object of the present invention to provide an article of clothing that is machine and/or hand washable.

It is an object of the present invention to provide an article of clothing that can be worn in multiple fashions by both men and women.

It is an object of the present invention to provide a brassiere that can provide an increase in support and lift to the breasts.

It is an object of the present invention to provide a shirt, pants, jacket, undergarment, and the like that has moisture management material that can be positioned between skin folds.

It is an object of the present invention to provide an undergarment that can be sized to be worn by adults and/or children.

It is an object of the present invention to provide an article of clothing that may have multiple pieces of moisture management material.

DESCRIPTION OF THE PREFERRED EMBODIMENTS

Figure 1A:
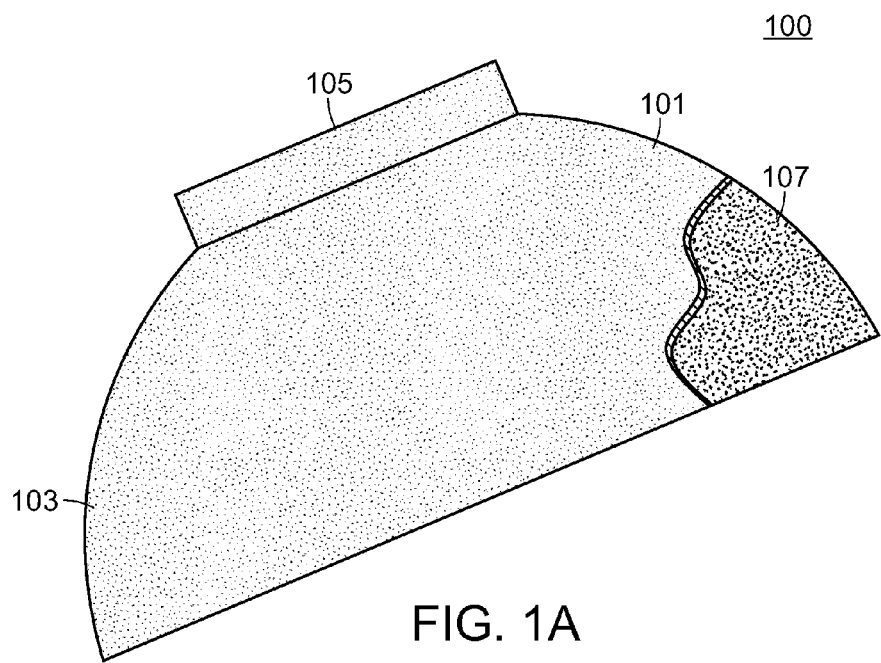
FIG. 1A is a perspective view of the moisture management material of an embodiment of the present invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Figure 1B:
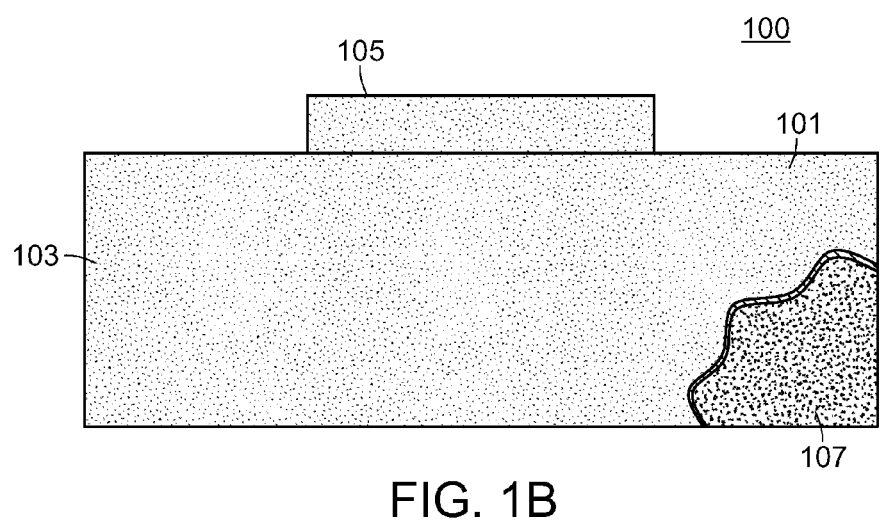
FIG. 1B is a perspective view of the moisture management material of another embodiment of the present invention.

Referring now to FIGS. 1A and 1B, there are multiple embodiments of the moisture management material 100 in accordance with the present invention. Generally, the moisture management material 100 has an outer layer 103 and an inner layer 107. The exact number of layers may vary and include up to about ten layers, but most all embodiments should provide for at least these two layers. These layers may be comprised of or combinations of the below materials and other material not explicitly listed herein. In some embodiments, medical grade fabrics and other medical grade materials. Such materials may have inherent antimicrobial, antibacterial, etc. properties or may be coated in such a material.

The outer layer 103 is preferably comprised of natural or synthetic textiles including but not limited to papers, woven, knitted, or non-woven fabrics, cloth, woven or non-woven fibers of wool, flax, rayon, cotton, bamboo, hemp, lyocell, and/or yarn, and synthetic textile including but not limited to microfibers, nylon, polyester, aramid fibers, olefins, and/or acrylic, or any combinations thereof.

The inner layer 107 is preferably comprised of natural or synthetic materials exhibiting hydrophilic properties including but not limited to spacer, natural rubber, polychloroprene, acrylonitrile butadiene, polyisoprene, polysiloxane, vinyl methyl silicone, polyurethane, fluoro silicone, polyester and other polyurethane foams, foam-backed fabrics, and the like or any combinations thereof.

The shape of the moisture management material 100 is largely dependent on the particular application for which it is to be employed. The overall shape of the moisture management material 100 may be polygonal or irregular. Generally, the moisture management material 100 has a body section 101 which comprises the main area of the material and a tab 105 extending therefrom. In many iterations that tab 105 is ancillary to the moisture management material 100 as a whole. The tab 105 provides a surface for coupling the moisture management material 100 to an article of clothing. The tab 105 may or may not have the multiple layers or the same arrangement of layers as the body section 101 of the moisture management material 100 and may not necessarily be moisture absorbent in and of itself.

In addition, the moisture management material 100 may be shaped and configured to reduce heat, friction, increase air circulation, and the like. Such factors will help to combat the environment which breeds the various afflictions described herein.

As shown, FIGS. 1A and 1B reflect differing shapes of the moisture management material 100. However, other shapes and sizes while not explicitly shown are contained under the purview of the present invention.

Figure 2A:
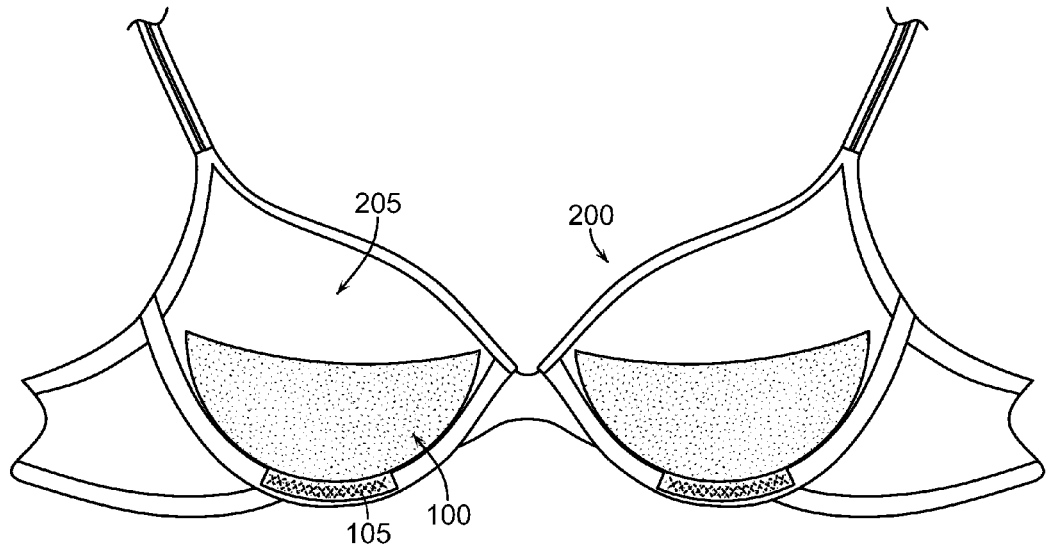
FIG. 2A is a rear view of a brassiere with the moisture management material coupled thereto and folded into the cups of the brassiere.
Figure 2B:
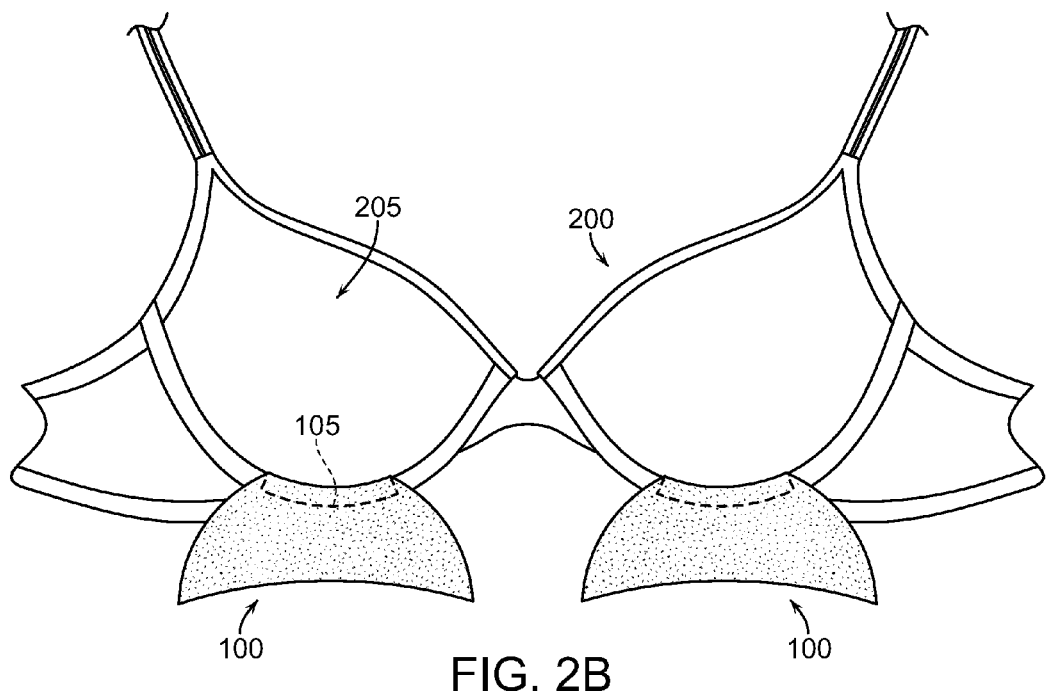
FIG. 2B is a rear view of a brassiere with the moisture management material coupled thereto and folded outwardly from the cups of the brassiere enabling the tucking between the bottom of the breast and the underbust.

In FIGS. 2A and 2B, there is one embodiment of the present invention acting as an accessory for a brassiere 200. This brassiere accessory can readily be coupled to either cup 205 or both cups 205 of the brassiere 200. Preferably, to seek maximum relief and protection from discomfort the moisture management material 100 may be coupled to each cup 205 of the brassiere 200 or in alternate embodiments the straps, bands, closures, or other components of the brassiere 200.

In FIG. 2A, the moisture management material 100 is sized and positioned to fit within each cup 205 of the brassiere 200. The tab 105 provides a surface for attachment to the brassiere 200. The tab 105 may be coupled by any appropriate mechanism including stitching, glues, epoxies, resins, chemicals, tapes, tacks, pins, clips, snaps, hook and loop fasteners (Velcro®), and the like or any combination thereof. It may also be appropriate to utilize a mechanism that allows for easy removal and replacement of the moisture management material 100. In some instances, the moisture management material 100 is permanently attached but may be machine and/or hand washable along with the brassiere 200. The tab 105 may further be covered by a layer of fabric that is also attached to the brassiere 200 to provide an additional layer of securement for the moisture management material 100 to the brassiere 200.

Figure 3A:
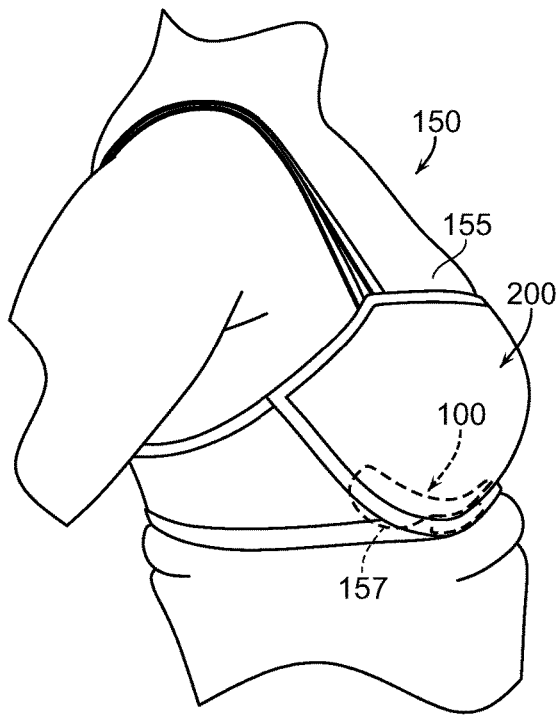
FIG. 3A is a side view of a user wearing an embodiment of the present invention with the moisture management material placed and/or tucked under the breast.
Figure 3B:
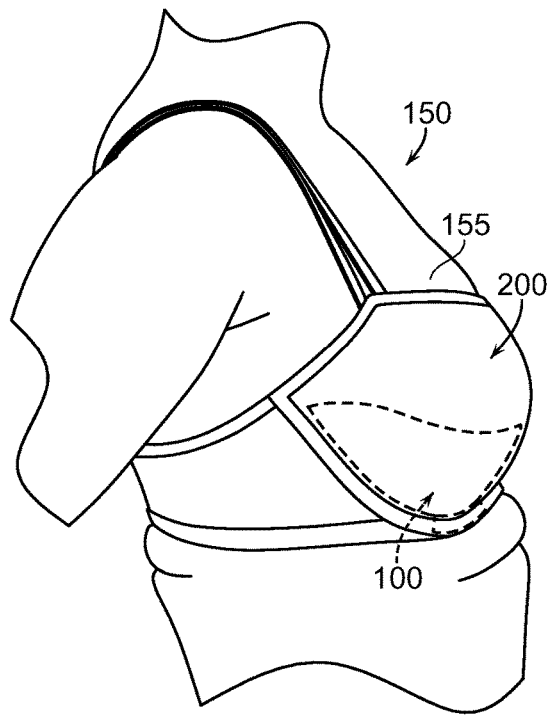
FIG. 3B is a side view of a user wearing an embodiment of the present invention with the moisture management material placed into the cup and supporting and lifting the breast.

In FIG. 3B, a user 150 is shown wearing the brassiere 200 in the configuration illustrated in FIG. 2A. Here, the moisture management material 100 is positioned within the cup 205 of the brassiere 200. When positioned on the user 150, the moisture management material 100 resides between the brassiere 200 and the breast 155 of the user 150. In this configuration, the moisture management material 100 provides an increase in support to the breast 155. This increase in support is noted by an increase in lift provided by the brassiere 200 and the moisture management material 100.

Referring now to FIG. 2B, the moisture management material 100 is shown in an alternate configuration. Here, the moisture management material 100 is positioned outwards from the cup 205 of the brassiere 200. The tab 105 still secures the moisture management material 100 in place in such a way as previously described.

In FIG. 3A, a user 150 is shown wearing the brassiere 200 in the configuration illustrated in FIG. 2B. Here, the moisture management material 100 has been positioned and folded outwardly from the brassiere 200. When wearing the brassiere 205 in this configuration, the user 150 places the moisture management material 100 between the breast 155 and the underbust 157, with the moisture management material 100 being tucked underneath the breast 155.

The underbust is the area located underneath where the breast would naturally "sit" or lie on the human torso and is where the underside of the breast would typically contact the skin of the torso when unsupported. The underbust terminates approximately where the breast and torso meet and outside the boundary of where the breast typically would contact the torso when unsupported. The moisture management material 100 can then prevent skin-on-skin contact in the underbust 157 as well as move or otherwise remove excess moisture such as from perspiration. This keeps the skin in this region dryer and limits environmental factors that many bacteria and fungus rely on for growth. The end result being a much greater decrease in the likelihood of infection, irritations, chaffing, intertrigo, discomfort, and the like.

Figure 3C:
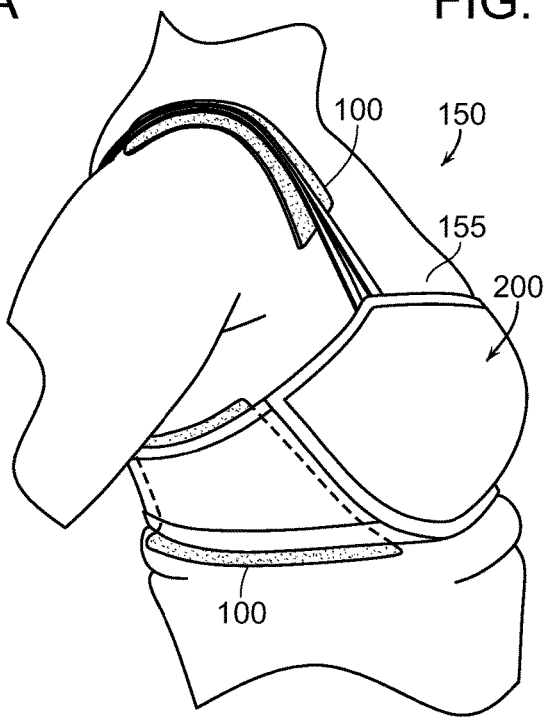
FIG. 3C is a side view of a user wearing an embodiment of the present invention with the moisture management material positioned under the straps, clasps, etc.

In FIG. 3C, there is an alternate embodiment of the brassiere 200 wherein the moisture management material 100 is positioned under the varying straps, clasps, and the like of the brassiere 200. Any of the embodiments shown in FIGS. 3A-C may be combined with one another in varying fashions to achieve the desired level of relief to the user 150.

In FIGS. 4-7 there are alternate embodiments of the present invention. As described in at least FIGS. 1A and 1B, any embodiment of the present invention, including those described in FIGS. 4-7 preferably has at least an inner layer, outer layer, body section, and tab. The exact shape and materials used in the execution may vary depending on individuals' various sizes, allergies, specific conditions or ailments, and the like. The usage of antimicrobial or antibacterial fibers such as metal infused fibers (i.e. copper, silver, zinc) is also contemplated when being used to combat or prevent certain infections, fungus, and bacterial afflictions.

Figures 4A, 4B:
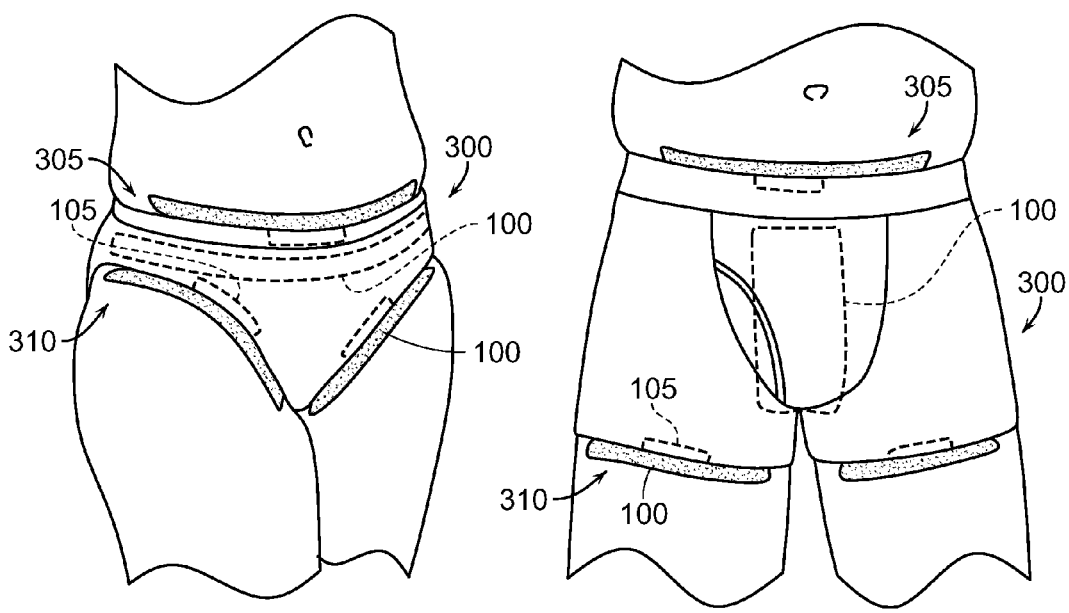
FIG. 4A is another embodiment of the present invention and is a front view of a female user wearing an embodiment of the present invention with multiple pieces of the moisture management material placed along the openings.
FIG. 4B is another embodiment of the present invention and is a front view of a male user wearing an embodiment of the present invention with multiple pieces of the moisture management material placed along the openings and over the groin area.

In FIG. 4A, there is an undergarment or underwear 300 which has various openings include at least a waistline 305 and leg openings 310. The underwear 300 is intended to at least partially cover the genital region of a user extending from about the waistline to upper thigh area of a user. The underwear 300 may be worn with various pieces of moisture management materials 100 coupled thereto. Here, there is a moisture management material positioned at the waistline 305 and each leg opening 310.

Referring now to FIG. 4B, the undergarment 300 is targeted towards men, as such the undergarment 300 may have a moisture management material 100 positioned inside the underwear 300. Such a location would enable the moisture management material 100 to be positioned underneath the man's testicles to prevent or limit any irritation, infection, or discomfort from occurring in such sensitive regions.

Further, in other embodiments, such a location would also enable the moisture management material 100 to be positioned underneath a man or a woman's loose lower abdomen or pannus, as shown in FIGS. 4A and 4B, often referred to as the "apron" to prevent or limit any irritation, infection, or discomfort from occurring in such sensitive regions.

Further, the moisture management material 100 may be repositionable so that it can be situated to reside between, for example, the leg openings 310 and the skin of the user, as well as at the waistline 305 of the user. The waistline 305 implementation may be particularly appropriate for users that are overweight and whose stomach area may fold over on itself above the underwear 300. Further, such a moisture management material 100 may fully encircle each of openings include those of the waistline 305 and/or legs 310. Thus, the size and shape of the moisture management material 100 may depend on the size and gender of the user, as well as the targeted area.

Figure 5:
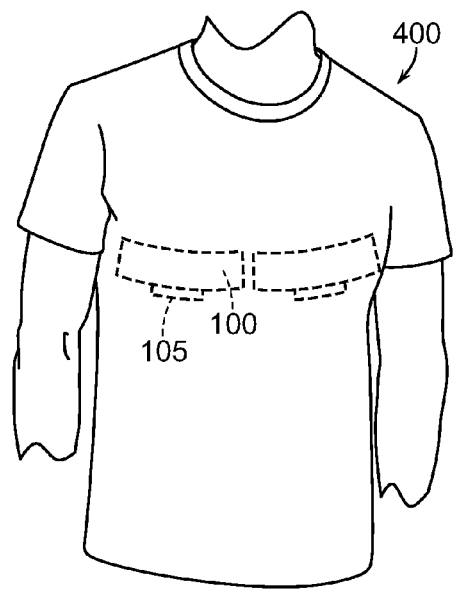
FIG. 5 is another embodiment of the present invention illustrating the moisture management material as shown in FIG. 1B coupled to a shirt.

In FIG. 5, there is a shirt 400 with the moisture management material 100 attached thereto. Such a shirt 400 may be sized to cover the torso region extending from about a neck of a user to about the waistline of the user or an extension beyond the torso. The shirt 400 may be particularly useful for male individuals or for females who do not or are not wearing a brassiere.

The moisture management material 100 may be coupled to the shirt 400 to be placed in the chest area. This allows the moisture management material 100 to be used in a similar fashion as described in the brassiere embodiment in FIGS. 2A and 2B. Further, the shirt 400 is shown utilizing the embodiment described in FIG. 1B. This particular embodiment may be more suitable for use by men as it provides appropriate coverage without needing to be constrained by a brassiere.

The moisture management material 100 can be tucked underneath the breast in the case of females, overweight males, and males exhibiting medical conditions such as gynecomastia. This allows for the movement of moisture and prevention of skin on skin contact. Other areas of interest in which moisture management material 100 can be positioned may be the armpits, near the waistline, or at strategically positioned places to target and prevent skin on skin contact, skin irritation, and general discomfort from the skin folds along the user's torso, or at the terminal end of the shirt 400.

Figure 6:
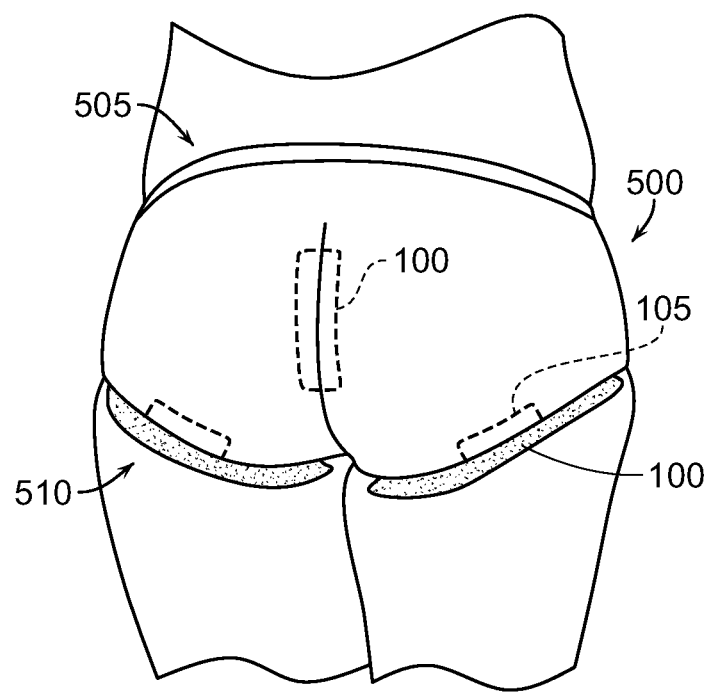
FIG. 6 is another embodiment of the present invention, shown from the rear, of a user wearing the embodiment of the present invention as an undergarment.

In FIG. 6, there is an embodiment of the present invention shown an undergarment such as a diaper or underwear or the like. The undergarment 500 with a waistband 505 and associated opening along with leg openings 510. In this embodiment, the moisture management material 100 may be placed along the various openings include the waistband 505 and/or leg openings 510, or along an interior surface (i.e. between buttocks) of the undergarment 500. Such an embodiment may be used with individuals of all age ranges who experience incontinence, irritation, and/or discomfort.

Figure 7:
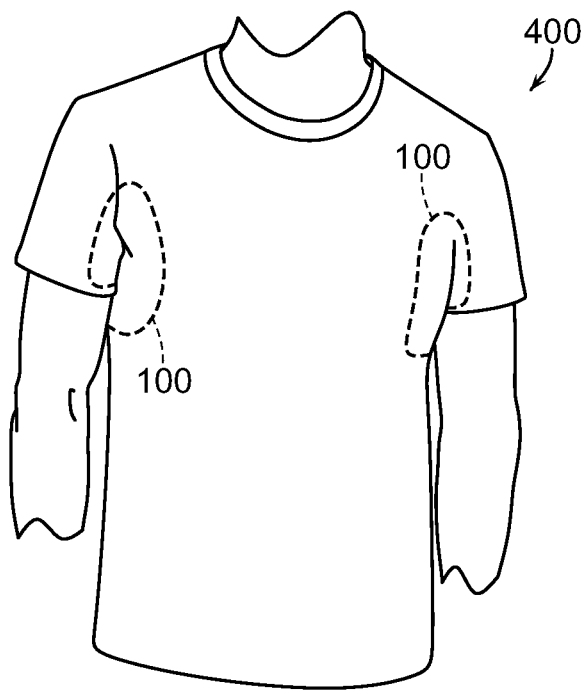
FIG. 7 is another embodiment of the present invention wherein the moisture management material is located under and around the underarm of a user.

In FIG. 7, there is another embodiment of the present invention showing the moisture management material 100 positioned under the "armpits" of the user. The shape of the moisture management material 100, in this embodiment, may reflect a crescent-like shape enabling full coverage of the underarm or armpit without interfering with the user.

The moisture management material 100 is attached in the same or a similar manner as previously described. The undergarment 500, in some embodiments, may be disposable or non-disposable diaper. The material of the undergarment may also aid in prevention of the buildup of undesirable moisture.

The present invention and its embodiments as described in FIGS. 1-7 may vary in size in accordance with manner of use and materials used. Preferably the moisture management material 100 when used in a brassiere 200, can be multiple shapes including but not limited to a semi-oval or semi-circle. The height and width of the moisture management material 100 in this embodiment is largely dependent on the breast or other body area to be relieved. Further, the moisture management material 100 may be washable, either by machine or by hand, to provide cleaning and prevent spreading of disease. In some instances, the entire embodiment is disposable. In other embodiments, the outer layer forms a sheath over the inner layer and the outer layer may be removed and discarded. In other embodiments, the layers are fused or otherwise adhered forming a single piece of material.

In other embodiments, the shape of the moisture management material 100 may vary and may not be the same as with the embodiment described above. For example, in the shirt 400 configuration, the moisture management material 100 may or may not be similar in shape to the brassiere 200 embodiment. However, the undergarment 500 and/or underwear 300 embodiment may have a moisture management material 100 that fully encircles a waistband or leg openings. This moisture management material 100 would then limit or prevent any type of chaffing, discomfort, or moisture issues from arising in these areas. Any such variations or implementations are clearly under the scope of this invention. Thus, the moisture management material may or may not be circular in shape and have multiple tabs or points of attachment to the article of clothing in any of the described embodiments.

Although this invention has been described with a certain degree of particularity, it is to be understood that the present disclosure has been made only by way of illustration and that numerous changes in the details of construction and arrangement of parts, as noted above and otherwise not mentioned, may be resorted to without departing from the intention and the scope of the invention.

What is claimed is:

1. A system to alleviate the occurrence of prolonged skin-on-skin contact, rashes, irritation, intertrigo, infections, discomfort, or chaffing or any combination thereof, the system comprising:
   a material forming an article of clothing; and
   a moisture management material comprising at least an outer layer, an inner layer, and at least one tab,
      wherein the inner layer comprises a hydrophillic foam backed fabric, and
      wherein the at least one tab extends from the moisture management material providing a surface to couple the moisture management material to the article of clothing.

2. The system of claim 1 wherein the outer layer comprises papers, woven, knitted, or non-woven fabrics, cloth, woven or non-woven fibers of wool, flax, rayon, cotton, bamboo, hemp, lyocell, yarn, microfibers, nylon, polyester, aramid fibers, olefins, acrylic, or any combinations thereof.

3. The system of claim 1 wherein the moisture management material is semi-oval in shape.

4. The system of claim 1 wherein the outer layer is configured to be removable from the inner layer.

5. The system of clothing of claim 1 wherein the moisture management material is configured to be positioned along a surface of a cup of a brassiere or between a breast and a skin surface of the user.

6. A medical accessory to alleviate the occurrence of prolonged skin-on-skin contact, rashes, irritation, intertrigo, infections, discomfort, or chaffing or any combination thereof, the medical accessory comprising:
   a semi-circular moisture management material having an inner layer, an outer layer, and at least a first edge and a second edge,
      wherein the first edge is a straight edge and the second edge is a curved edge,
      wherein the outer layer comprises antimicrobial fibers and the inner layer comprises a hydrophilic foam backed fabric; and
   at least one tab extending from the curved edge of the moisture management material sized to enable the medical accessory to be coupled to an article of clothing.

7. The medical accessory of claim 6 wherein a portion of the moisture management material is coupled to a brassiere and sized to be capable of being folded into a cup of the brassiere.

8. The medical accessory of claim 6 wherein a portion of the moisture management material is configured to be positioned between a breast and an underbust of a user.

9. The medical accessory of claim 7 wherein the medical accessory is permanently or removably coupled to the brassiere.

10. The medical accessory of claim 7 wherein the moisture management material is coupled to the brassiere above a top surface and/or below a bottom surface of any one of an underwire, straps of the brassiere, cups of the brassiere, clasps of the brassiere, or a combination thereof.

11. A brassiere accessory comprising:
   a moisture management material having one flat straight edge and one curved edge,
      wherein the moisture management material has at least an inner layer and an outer layer,
         wherein the inner layer is bounded on both sides by the outer layer, and
         wherein the inner layer comprises a hydrophillic foam backed fabric;
   at least one tab extending from the curved edge of the moisture management material, the at least one tab being sized to enable the brassiere accessory to be coupled to a brassiere,
      wherein the moisture management material is configured to be positioned into a cup of the brassiere or positioned to extend outwardly from the cup of the brassiere,
      wherein when the moisture management material is positioned in the cup of the brassiere, the moisture management material is configured to support and lift a breast of a user, and
      wherein when the moisture management material is positioned to extend outwardly from the cup, the moisture management material prevents skin on skin contact; and
   wherein if the brassiere has an underwire the tab is coupled to the brassiere above and/or below the underwire, and if the brassiere has no underwire the tab is coupled to a fabric strip of the brassiere.

12. The brassiere accessory of claim 11 wherein the moisture management material, when folded outwardly from the cup of the brassiere and positioned between the breast and an underbust of a user alleviates rash, chaffing, irritation, intertrigo, infections, discomfort, or any combination thereof.

13. The brassiere accessory of claim 11 wherein the moisture management material and tab is a unitary piece.

* * * * *